United States Patent [19]

Eisenbarth et al.

[11] Patent Number: 5,003,017

[45] Date of Patent: Mar. 26, 1991

[54] HEAT-CURABLE BISMALEIMIDE-ALKENYL HETEROCYCLIC MOLDING MATERIAL

[75] Inventors: Philipp Eisenbarth, Bad Duerkheim; Gerd Linden, Heidelberg; Volker Altstaedt, Gernsheim; Roland Peter, Mutterstadt, all of Fed. Rep. of Germany

[73] Assignee: BASF Aktiengesellschaft, Ludwigshafen, Fed. Rep. of Germany

[21] Appl. No.: 384,837

[22] Filed: Jul. 26, 1989

[30] Foreign Application Priority Data

Aug. 10, 1988 [DE] Fed. Rep. of Germany ....... 3827120

[51] Int. Cl.$^5$ ............................................. C08F 22/40
[52] U.S. Cl. .................................... 526/262; 526/263; 528/170; 528/322
[58] Field of Search .............. 526/262, 263; 528/322, 528/170

[56] References Cited

U.S. PATENT DOCUMENTS

| 3,742,141 | 5/1988 | Dien et al. | 526/262 |
| 4,849,485 | 7/1989 | Pockett | 526/262 |
| 4,921,931 | 5/1990 | Wang | 526/262 |

*Primary Examiner*—Harold D. Anderson
*Attorney, Agent, or Firm*—William G. Conger

[57] ABSTRACT

Heat-curable bismaleimide resins contain a bismaleimide and a heterocyclic comonomer having terminal alkenyl or alkenyloxy groups. A preferred comonomer is 2,6-bis-(2-propenylphenoxy)-pyridine. The bismaleimide resins are suitable for the production of high performance composites.

2 Claims, No Drawings

HEAT-CURABLE BISMALEIMIDE-ALKENYL HETEROCYCLIC MOLDING MATERIAL

The present invention relates to heat-curable resins based on bismaleimides.

Although bismaleimide resins which contain aromatic diamines as comonomers have excellent mechanical and electrical properties after curing, even at above 200° C., they have poor solubility in conventional solvents and their cured products are very brittle.

Their relatively high softening temperatures coupled with high melt viscosities are further advantages; semifinished products or prepregs produced from these resins do not have the tack frequently desired by the processor.

Lower viscosities are obtained by the use of binuclear allylphenols or etherified allylphenols, as described in, for example, U.S. Pat. No. 4,100,140. Because of the relatively short chain length and the resultant relatively large proportion of aliphatic structural elements, however, these resins are not sufficiently stable to thermal oxidation for many applications. Moreover, catalysts, for example tertiary amines, have to be used in order to achieve short curing times; the corresponding semifinished products frequently do not have tack sufficient for the processor.

Bismaleimide resins which contain polynuclear aromatic comonomers having terminal alkenylene groups are described in European Patent 230,741. The comonomers used there either lead, because of the excessively high aliphatic content, to resins having insufficient stability to thermal oxidation (comonomers of type IIa according to European Patent 230,741) or give resins having relatively high softening points or melt viscosities (comonomers of type IIb-e according to European Patent 230,741). The addition of catalysts is recommended for accelerating curing.

It is an object of the present invention to provide bismaleimide resins which are without some or all of the stated disadvantages.

We have found that this object is achieved by the novel resins, which contain heterocyclic comonomers. They have excellent tack at room temperature, coupled with a low viscosity. Because of their nitrogen-containing molecular structure, these resins cure rapidly, even without the addition of catalysts, at elevated temperatures, and give crosslinked polymers having high heat resistance, good toughness and relatively low water absorption. The advantageous viscosity properties permit the use of modern processing methods, for example filament winding or resin transfer molding.

The heterocyclic comonomers which can be used according to the invention have the general formula I

where R is alkenyl of 3 to 6 carbon atoms or a corresponding alkenyloxy group. Allyl, propenyl and allyloxy groups are preferred.

Ar is a mononuclear or binuclear aromatic radical, for example phenylene, naphthylene or phenylene-Xphenylene (where X is a chemical bond or a divalent group, for example O, S, SO$_2$, CO or C(R$^1$)$_2$ in which R$^1$ is H, C$_1$-C$_6$-alkyl, aryl or CF$_3$) o-Phenylene, m-phenylene and p-phenylene are preferred.

Ar may furthermore possess an OH group, in addition to the alkenyl group R.

The heterocyclic radical Het is a nitrogen-containing, aromatic six-membered ring selected from the group consisting of

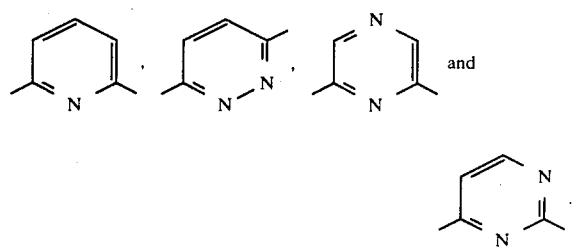

The pyridine and pyridazine rings are preferred.

For the preparation of the comonomers which can be used according to the invention, a dihaloheterocycle Hal—Het—Hal is condensed with 2 equivalents of a bis-phenol HO—Ar—OH in the presence of a base by a known method, for example according to DE-A 19 34 889, with formation of a heterocyclic phenol II.

Suitable dihaloheterocycles are 2,6-dichloropyridine, 3,6-dichloropyridazine, 2,6-dichloropyrazine and 2,6-dichloropyrimidine. Suitable bisphenols are, for example, hydroquinone, resorcinol and bisphenol A; further bisphenols are mentioned in DE-A 19 34 889.

The heterocyclic bisphenols II are then etherified, for example according to DE-A 28 18 091, with an alkenyl halide. Preferred alkenyl halides are allyl chloride, allyl bromide and methallyl chloride.

This may be followed by a Claisen rearrangement reaction, likewise according to DE-A 28 18 091, the corresponding OH-containing comonomers (orthoallyl-phenols) being obtained; these can furthermore be converted into the propenylphenols, which are likewise novel, by base catalysis according to EP-A 14 816.

Comonomers which can be prepared in this manner are, for example, 2,6-bis-(3-allyl-4-hydroxyphenoxy)-pyridine, 2,6-bis-(3-allyloxyphenoxy)-pyridine, 2,6-bis-(4-allyl-3-hydroxyphenoxy)-pyridine, 2,6-bis-[(3-allyl-4-hydroxyphenylisopropyl)-phenoxy]-pyridine and the corresponding pyridazine derivatives.

An alternative method for the preparation of comonomers of the formula I is the condensation of one of the two stated dihaloheterocycles Hal-Het-Hal with 2 equivalents of an alkenylphenol HO-Ar-R by a known method. Examples of suitable alkenylphenols are 2-allyl-phenol, 2-propenylphenol and eugenol.

A comonomer which can be prepared in this manner and is preferably used is 2,6-bis-(2-propenylphenoxy)-pyridine. This heterocyclic compound is novel.

The novel bismaleimide resins are obtained by reacting the heterocyclic alkenyl compound with a bis-maleimide of the general formula

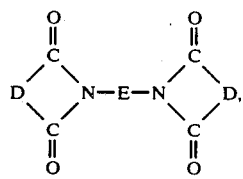

where D is an unsubstituted or substituted carbon double bond and E is a divalent radical of two or more carbon atoms. Bismaleimides are disclosed in, for example, DE-A-2 040 094, DE-A-2 719 903 and DE-A-3 247 058. In addition to bismaleimides, polymaleimides and mixtures of various bismaleimides are in principle also suitable. Preferred bismaleimides are 4,4'-bismaleimidodiphenylmethane, 4,4'-bismaleimidodiphenyl ether, 3,3'-bismaleimidodiphenyl sulfone, 1,3-bis-maleimidobenzene, 2,4-bis-maleimidotoluene, 1,6-bis-maleimidohexane and 2,2,4-tri-methyl-1,6-bis-maleimidohexane. Up to 20% by weight of a monoimide may also be present.

For the preparation of the novel bismaleimide resins, the starting materials are mixed using a conventional technique and are heated to 70°–190° C., a prepolymer being formed. Depending on the progress of the prepolymerization, the result is a melt having a relatively low viscosity or a glassy solid which, depending on the intended use, is milled or is dissolved in a solvent. The preparation of the resins can also be carried out in the presence of a solvent.

The mixing ratio in the reaction of the bismaleimide with the heterocyclic alkenyl compound can be chosen relatively freely, the ratio of the number of equivalents preferably being from 1:0.05 to 1:5.

Depending on the intended use, it may be advantageous to add further components to the novel resins. Examples of suitable additional components are amines, preferably aromatic diamines (e.g. 4,4'-diaminodiphenyl-methane) and aminophenols, which are also capable of undergoing an addition reaction with the maleimide double bonds. It is also possible to use prepolymers, for example those obtained from a bisimide and an amine.

For certain applications, it may also be advantageous to use suitable vinyl monomers, for example styrene, α-methylstyrene, divinylbenzene, acrylates, methacrylates, diallyl phthalate, 3,3'-diallylbisphenol A, triallyl isocyanurate, triallyl cyanurate or vinyl-pyrrolidone, to obtain the desired viscosity.

The novel mixtures may contain inhibitors as further additives. Suitable inhibitors are hydroquinone, benzoquinone and phenothiazine. The amount of inhibitors used should be about 0.05–1.5% by weight.

The novel mixtures may contain further additives which are conventionally used in the technology of curable plastics, for example fillers, plasticizers, pigments, dyes, mold release agents or flame-retardant substances. Glass fibers, carbon fibers, graphite powder, mica, quartz powder, kaolin or metal powder may also be used as fillers, in an amount of not more than 80% by weight, based on the mixture.

The novel mixtures can be used as impregnating, casting and laminating resins or as molding materials (with or without fillers).

If they are used for the production of high performance composites, impregnation of glass fibers, carbon fibers or Aramid fibers can be carried out with formation of unidirectional or fabric prepregs, either from the melt at 50°–150° C. or from solution. Suitable solvents are halohydrocarbons, eg. dichloromethane, ketones, eg. acetone or methyl ethyl ketone, glycol esters, toluene, dimethylformamide, N-methylpyrrolidone or mixtures of a plurality of solvents.

The novel resins are cured at about 100°–300° C., preferably 160°–260° C., under atmospheric or superatmospheric pressure. The curing temperature selected depends decisively on the length of the curing time, and vice versa. Gradual curing is often advantageous, crosslinking of the polymers being induced at a lower temperature, initially with shaping. Removal from the mold can then be followed by postcuring at above 200° C., if necessary for several hours, to effect complete curing.

The novel resins can be used to produce high performance materials, for example insulating materials, structural components, instrument housings and electrical components, which are exposed to high temperatures.

EXAMPLE 1

(a) Preparation of 2,6-bis-(2-propenylphenoxy)-phenoxy)-pyridine

A mixture of 296 g of 2,6-dichloropyridine, 537 g of 2-allylphenol, 304 g of potassium carbonate, 2,000 ml of N-methylpyrrolidone and 400 ml of chlorobenzene was heated at 190° C. for 21 hours, the water of reaction formed being distilled off azeotropically. Thereafter, about 4 l of water were added to the reaction mixture, which was extracted with 4 l of dichloromethane. The combined organic phases were washed with water in a liquid/liquid extractor, dried over sodium sulfate and evaporated down under reduced pressure. 601.9 g (88%) of product were obtained as a brownish oil, which crystallizes slowly when left to stand for a long time (colorless crystals of melting point 69°–73° C.); $^1$H-NMR: 1.75 (d, 6H, CH$_3$), 5.60–5.80 (m, olef. H, small amount of cis-isomer), 6.20–6.50 (m, 6H, olef. and arom. H), 7.00–7.80 (m, 9H, arom.).

(b) Preparation of a bismaleimide resin 371 g of Compimide 353 (monomer-containing bismaleimide resin, commercial product from Technochemie Verfahrenstechnik, Dossenheim) and 200 g of 2,6-bis-(2-propenylphenoxy)-pyridine were melted together at 140° C. while stirring, heated for a further 15 minutes and then further processed as follows:

Some of the resin was poured onto a metal foil for faster cooling. The resin was very tacky at room temperature and had a viscosity of 2320 mPa.s at 75° C. The gelling time at 160° C. was 25 minutes.

The remaining part of the resin was poured into metal molds measuring 30×30×0.4 or 0.1 cm and cured in each case for 2 hours at 160° C. and at 190° C. and for 10 hours at 240° C. At 282° C., the polymer still had shear modulus corresponding to 50% of its room temperature shear modulus (25° C.: 1,400 N/mm$^2$, measured according to DIN 53,455). The modulus of elasticity was 3,600 N/mm$^{-2}$ (according to DIN 53,457) and the impact strength was 8.2 kJ.m$^{-2}$ (according to DIN 53,453). After the resin had been stored in water at 70° C. for 8 days, the water absorption was 4.21%.

(c) Production of a unidirectional prepreg or laminate

For the preparation of a unidirectional prepreg using the carbon fiber Torayca T 800 (Toray, Japan), the bismaleimide resin according to 1b) was first applied at about 65° C. to a continuously moving prepreg paper with formation of a resin film about 60 μm thick, and the fiber belt, having a weight per unit area of 135 g/m$^2$, was then placed in the resin film at about 80° C. under pressure and was completely impregnated. The resin content of the prepreg obtained in this manner was 35%, corresponding to a nominal prepreg thickness of 0.125 mm, based on a fiber content of 60% by volume.

The prepreg had very good tack and was easily drapable; its resin-glass temperature was 4° C. (determined by DSC).

For the preparation of a unidirectionally reinforced high performance composite, laminates were produced by placing a plurality of prepreg layers one on top of the other (corresponding to the requirement of the test specimen standard) and were cured using the curing cycle stated under lb). The laminate had a GIc value of 262 kJ/m² (according to NASA test standard RP 10920).

EXAMPLE 2

(a) Preparation of 2,6-bis-(3-allyloxyphenoxy)-pyridine 59.7 g allyl chloride were added dropwise at 95° C. to a solution of 87.9 g of 2,6-bis-(3-hydroxyphenoxy)-pyridine (prepared according to DE-A 19 34 889 from 2,6-dichloropyridine and 2 moles of resorcinol; colorless crystals of melting point 188° C.) and 26.4 g of sodium hydroxide in 500 ml of n-propanol. The mixture was refluxed for a further 10 hours and then cooled to room temperature, after which 500 ml of dichloromethane were added and the precipitated sodium chloride was filtered off. After the solvent had been distilled off under reduced pressure, 101 g (90%) of product were obtained as a yellowish oil having a viscosity of 60 mPa.s at 50° C.; NMR (300 MHZ, D6-DMSO): 4.56 (d, 4H, allyl), 5.22-5.42 (dd, 4H, allyl), 5.95-6.10 (m, 2H, allyl), 6.60-6.85 (m, 6H, arom.), 7.22 (t, 2H, arom.), 7.82 (t, 1H, arom.).

(b) Preparation of 2,6-bis-[4(2)-allyl-3-hydroxyphenoxy)-pyridine 64 g of the allyl ether from Example 2a) were heated at 190° C. for 5 hours. Yield: 63 g (97%).

(c) Preparation of a bismaleimide resin

A bismaleimide resin, which was very tacky at room temperature and had a viscosity of 2,100 mPa.s at 75° C., was prepared from 70 g of 4,4'-bismaleimidodiphenyl-methane and 30 g of the allyl ether from Example 2b), similarly to Example 1. Curing similarly to Example 1 gave a polymer which, at 290° C, still had a shear modulus which corresponded to 50% of its room temperature shear modulus (25° C.: 1,500 N/mm², according to DIN 53,445).

EXAMPLE 3

(a) Preparation of 3,6-bis-(2-propenylphenoxy)-pyridazine

A mixture of 149 g of 3,6-dichloropyridazine, 268.4 g of 2-allylphenol, 152 g of potassium carbonate, 400 ml of N-methylpyrrolidone and 900 ml of toluene was heated at 140° C. for 30 hours, the resulting water of reaction being distilled off azeotropically. Working up similarly to Example la) gave 317 g (92%) of a partially crystalline product, which consisted of an isomer mixture of allyl-containing and propenyl-containing products. After the addition of methanol and filtration, 140 g of pure 3,6-bis-(2-propenylphenoxy)-pyridazine were obtained as colorless crystals of melting point 165°-168° C.; ¹H-NMR: 1.80 (d, CH ), 5.70-5.90 (m, small amount of cis-isomer), 6.20-6.50 (m, 4H, olef.) 7.0-7.7 (m, 1OH, arom.).

(b) Preparation of a bismaleimide resin

A resin was prepared from 60 g of Compimide 353, 40 g of 3,6-bis-(2-propenylphenoxy)-pyridazine and 15 g of diallyl phthalate and was further processed, these steps being carried out similarly to Example la); the resin had a viscosity of 3,600 mPa.s and was very tacky at room temperature. Curing similarly to Example 1 gave a polymer which, at 283° C., still had a shear modulus corresponding to 50% of its room temperature shear modulus (25° C.: 1350 N/mm,, according to DIN 53,445).

We claim:

1. A heat-curable bismaleimide resin forming composition, containing
A. a bismaleimide and
B. a heterocyclic comonomer of the formula

where R is an alkenyl or alkenyloxy group of 3 to 6 carbon atoms, Ar is an unsubstituted or hydroxyl substituted phenylene, naphthylene or

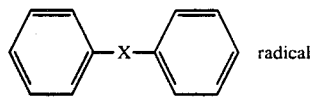

in which X is O, S, SO₂, CO, C(R¹)₂, where R¹ is H, C₁-C₆-alkyl, CF₃ or phenyl, or where X is a chemical bond, and Het is a six-membered deterocyclic ring selected from the group consisting of

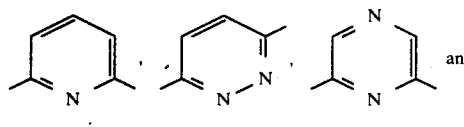

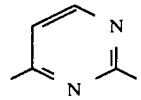

2. A heat-curable bismaleimide resin forming composition as claimed in claim 1, where R is propenyl, Ar is 1,2-phenylene; and Het is a 2,6-pyridine radical.

* * * * *